United States Patent
Tsutsumi et al.

(10) Patent No.: US 6,315,736 B1
(45) Date of Patent: Nov. 13, 2001

(54) ANESTHETIC-DEPTH MONITOR APPARATUS

(75) Inventors: Yoshiaki Tsutsumi, Inuyama; Hideichi Tsuda, Komaki, both of (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/580,647

(22) Filed: May 30, 2000

(30) Foreign Application Priority Data

Jun. 9, 1999 (JP) .................................................. 11-162368

(51) Int. Cl.[7] ............................... A61B 5/02; A61B 5/103
(52) U.S. Cl. ............................................. 600/500; 600/587
(58) Field of Search ..................................... 600/500, 546, 600/554, 587, 481, 544, 545, 485

(56) References Cited

U.S. PATENT DOCUMENTS

| 4,570,640 | * | 2/1986 | Barsa | 600/554 |
|---|---|---|---|---|
| 4,788,982 | * | 12/1988 | Gedeon et al. | 600/483 |
| 5,195,531 | * | 3/1993 | Bennett | 600/546 |
| 5,871,450 | | 2/1999 | Nomura et al. . | |
| 5,964,713 | | 10/1999 | Nomura et al. . | |
| 6,117,075 | * | 9/2000 | Barnea | 600/300 |

* cited by examiner

Primary Examiner—Eric F. Winakur
Assistant Examiner—Navin Natnithithadhi
(74) Attorney, Agent, or Firm—Oliff & Berridge, PLC (57) ABSTRACT

An apparatus for monitoring an anesthetic depth of a living subject, including at least two devices of (a) an arousal-index determining device which determines an arousal index indicating a degree of arousal of the subject, (b) a pain-index determining device which determines a pain index indicating a degree of pain of the subject, and (c) a muscular-relaxation-index determining device which determines a muscular-relaxation index indicating a degree of muscular relaxation of the subject, and an anesthetic-depth determining device for determining, based on at least two indexes determined by the at least two devices, an anesthetic depth of the subject according to a predetermined relationship between anesthetic depth and the at least two indexes.

11 Claims, 7 Drawing Sheets

ANESTHETIC-DEPTH MONITOR APPARATUS

BACKGROUND OF THE INVENTION

1. Field of the Invention

The present invention relates to an anesthetic-depth monitor apparatus which monitors an anesthetic depth of a living subject who is undergoing a surgical operation. The anesthetic depth means a degree of suppression of pain or consciousness of the subject.

2. Related Art Statement

It is desirable that the degree of anesthesia of a patient who is undergoing a surgical operation be not too shallow nor too deep, that is, be kept at an appropriate level. To this end, it has conventionally been practiced to monitor the anesthetic depth of a patient by measuring the change of his or her blood pressure, heart rate, or respiration rate in response to the surgical stimuli, or observing his or her cilium reflex or pupil's diameter, or the color or temperature of his or her limb or peripheral body portion. In addition, U.S. Pat. Nos. 5,871,450 and 5,964,713, assigned to the Assignee of the present application, disclose an anesthetic-depth measuring device which determines an anesthetic depth based on the ratio of peripheral body temperature to deep body temperature, and an anesthetic-depth measuring device which determines an anesthetic depth based on the fluctuations of pulse period or blood pressure.

However, in some cases, the conventional devices may not enjoy the highest reliability. For example, in the case where a conventional device is used to monitor the anesthetic depth of a patient to keep it at an appropriate level, the anesthesia may not be kept sufficiently deep so that the patient may be awaken, which causes the patient to feel much discomfort. To avoid this, it is likely to administer, in an actual surgical operation, too much anesthetic agent to the patient. However, the administration of too much anesthetic agent delays the awakening of the patient after the operation. In addition, the consumption of too much anesthetic agent is not economical.

SUMMARY OF THE INVENTION

It is therefore an object of the present invention to provide an anesthetic-depth monitor apparatus which can monitor, with high reliability, an anesthetic depth of a living subject who is undergoing a surgical operation.

The Inventors have carried out extensive studies and researches, and have found the following facts: The objects of general anesthesia include not only the above-indicated suppression of consciousness and pain but also the relaxation of muscles. Those three items, that is, the suppression of consciousness, the suppression of pain, and the muscular relaxation are related to one another. For example, when a patient has consciousness, he or she feels strong pain, whereas a patient may not physically react, because of his or her muscular relaxation, against pain though he or she has consciousness. Therefore, it is desirable that the anesthetic depth be monitored by using at least two items of the above-indicated two items. However, each of the conventional anesthetic-depth measuring devices or methods measures an anesthetic depth based on only one of the three items, and accordingly may not have enjoyed the highest reliability. For example, the conventional method in which anesthetic depth is monitored based on change of blood pressure of a patient in response to surgical stimuli, is related to only the suppression of pain; and the anesthetic-depth measuring devices disclosed in the above-indicated U.S. Patents is related to only the level of activity of nerve, i.e., the suppression of consciousness or the degree of arousal. The present invention has been developed based on these findings.

(1) According to a first feature of the present invention, there is provided an apparatus for monitoring an anesthetic depth of a living subject, comprising at least two devices of (a) an arousal-index determining device which determines an arousal index indicating a degree of arousal of the subject, (b) a pain-index determining device which determines a pain index indicating a degree of pain of the subject, and (c) a muscular-relaxation-index determining device which determines a muscular-relaxation index indicating a degree of muscular relaxation of the subject; and an anesthetic-depth determining means for determining, based on at least two indexes determined by the at least two devices, an anesthetic depth of the subject according to a predetermined relationship between anesthetic depth and the at least two indexes.

According to this feature, the anesthetic-depth monitor apparatus determines an anesthetic depth of the subject based on at least two of the arousal index, the pain index, and the muscular-relaxation index of the subject. Therefore, the present apparatus can determine a highly reliable anesthetic depth.

(2) According to a second feature of the present invention, there is provided an apparatus for monitoring an anesthetic depth of a living subject, comprising an arousal-index determining device which determines an arousal index indicating a degree of arousal of the subject; a pain-index determining device which determines a pain index indicating a degree of pain of the subject; a muscular-relaxation-index determining device which determines a muscular-relaxation index indicating a degree of muscular relaxation of the subject; and an anesthetic-depth determining means for determining, based on the determined arousal index, the determined pain index, and the determined muscular-relaxation index, an anesthetic depth of the subject according to a predetermined relationship between (A) anesthetic depth and (B) (b1) arousal index, (b2) pain index, and (b3) muscular-relaxation index.

According to this feature, the anesthetic-depth monitor apparatus determines an anesthetic depth of the subject based on the arousal index, the pain index, and the muscular-relaxation index of the subject. Therefore, the present apparatus can determine a very highly reliable anesthetic depth.

(3) According to a third feature of the present invention that includes the first or second feature (1) or (2), the monitor apparatus comprises the arousal-index determining device, and the arousal-index determining device comprises a pulse-wave sensor which detects a pulse wave including a plurality of heartbeat-synchronous pulses each of which is produced in synchronism with a heartbeat of the subject; pulse-period-relating-information obtaining means for successively obtaining a batch of pulse-period-relating information relating to a pulse period at which the each heartbeat-synchronous pulse is produced in synchronism with the heartbeat of the subject; means for determining a magnitude of a high-frequency component of fluctuations of the batches of pulse-period-relating information successively obtained by the pulse-period-relating-information obtaining means, the high-frequency component having a high frequency substantially equal to a frequency of respiration of the subject; means for determining a magnitude of a low-frequency component of the fluctuations of the batches of pulse-period-relating information, the low-frequency component having a low frequency substantially equal to a predetermined fraction of the frequency of respiration of the subject; and means for determining the arousal index based on a ratio of the magnitude of the low-frequency component to the magnitude of the high-frequency component.

(4) According to a fourth feature of the present invention that includes any one of the first to third features (1) to (3), the monitor apparatus comprises the pain-index determining device, and the pain-index determining device comprises a pulse-wave sensor which detects a pulse wave including a plurality of heartbeat-synchronous pulses each of which is produced in synchronism with a heartbeat of the subject; pulse-period-relating-information obtaining means for successively obtaining a batch of pulse-period-relating information relating to a pulse period at which the each heartbeat-synchronous pulse is produced in synchronism with the heartbeat of the subject; pulse-period-relating-information-change determining means for determining a change of the batches of pulse-period-relating information successively obtained by the pulse-period-relating-information obtaining means; and means for determining the pain index based on the change determined by the pulse-period-relating-information-change determining means.

(5) According to a fifth feature of the present invention that includes any one of the first to fourth features (1) to (4), the monitor apparatus comprises the muscular-relaxation-index determining device, and the muscular-relaxation-index determining device comprises a stimulating device which applies a stimulus to a body portion of the subject; a motion sensor which detects a motion of the body portion of the subject in response to the stimulus applied by the stimulating device; and means for determining the muscular-relaxation index based on a magnitude of the motion detected by the motion sensor.

(6) According to a sixth feature of the present invention that includes any one of the first to fifth features (1) to (5), the monitor apparatus further comprises a display device which displays the at least two indexes determined by the at least two devices.

(7) According to a seventh feature of the present invention that includes any one of the first to sixth features (1) to (6), the monitor apparatus further comprises a display device which displays the anesthetic depth determined by the anesthetic-depth determining means.

(8) According to an eighth feature of the present invention that includes any one of the third to seventh features (3) to (7), the pulse-wave sensor comprises an electrocardiograph which includes a plurality of electrodes adapted to be worn on the subject and which detects an electrocardiogram from the subject via the electrodes.

(9) According to a ninth feature of the present invention that includes the second feature (2), the monitor apparatus further comprises a display device which displays, in a three-dimensional graph having a first axis indicative of arousal index, a second axis indicative of pain index, and a third axis indicative of muscular-relaxation index, the arousal index determined by the arousal-index determining device, the pain index determined by the pain-index determining device, and the muscular-relaxation index determined by the muscular-relaxation-index determining device.

(10) According to a tenth feature of the present invention that includes any one of the first to ninth features (1) to (9), the anesthetic-depth determining means comprises means for determining the anesthetic depth based on a product of said at least two indexes determined by said at least two devices.

(11) According to an eleventh feature of the present invention that includes the second feature (2), the anesthetic-depth determining means comprises means for determining the anesthetic depth based on a product of the determined arousal index, the determined pain index, and the determined muscular-relaxation index.

BRIEF DESCRIPTION OF THE DRAWINGS

The above and optional objects, features and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
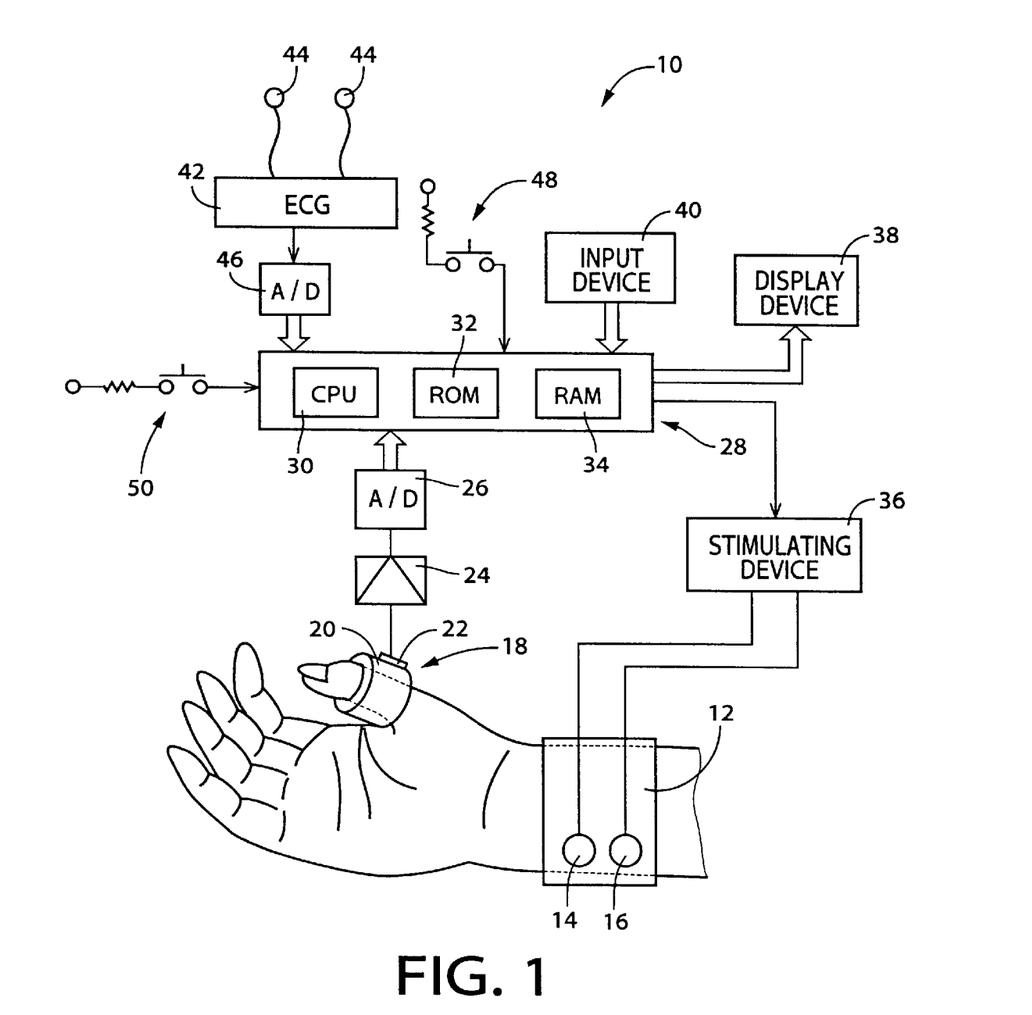
FIG. 1 is a diagrammatic view for explaining the construction of an anesthetic-depth monitor apparatus to which the present invention is applied.

Referring first to FIG. 1, there is shown an anesthetic-depth monitor apparatus 10 embodying the present invention.

In FIG. 1, reference numeral 12 designates a wrist band which is provided with a pair of metallic electrodes 14, 16 and which is wound around a wrist of a patient as a living subject so that the two electrodes 14, 16 are pressed, with an appropriate pressure, against the skin under which an ulnar nerve runs along an ulna. The wrist band 12 is provided by a stretchable annular belt, or a band-like belt having a fastener for connecting opposite end portions thereof to each other.

A cuff 18 includes an air bag which is provided by a flexible material such as a resin sheet and in which air is tightly enclosed; and a pressure sensor 22 which detects an air pressure in the air bag 20. The cuff 18 is wound around a thumb of the patient. Like the wrist band 12, the cuff 18 is provided by a stretchable annular belt, or a band-like belt having a fastener for connecting opposite end portions thereof to each other.

The pressure sensor 22 produces a pressure signal representing the detected air pressure in the air bag 20 (hereinafter, referred to as the "cuff pressure"), and supplies the pressure signal to a control device 28 via a signal amplifying and filtering circuit 24 and an analog-to-digital ("A/D") converter 26. The signal amplifying and filtering circuit 24 has a specific signal-filtering frequency band corresponding to the changes of the cuff pressure caused by the reaction of the thumb in response to the external stimuli applied to the wrist. That is, the filtering circuit 24 transmits only signal components having frequencies falling within the specific signal-filtering frequency band, but does not transmit the other signal components.

The control device 28 is provided by a microcomputer which includes a central processing unit (CPU) 30, a read only memory (ROM) 32, a random access memory (RAM) 34, and an input and output (I/O) port (not shown). The CPU 30 processes input signals according to control programs pre-stored in the ROM 32 by utilizing a temporary-storage function of the RAM 34, and outputs drive signals to a stimulating device 36 to stimulate the wrist's skin under which the ulnar nerve runs, and to a display device 38 to display an anesthetic depth measured by the present monitor apparatus 10.

An input device 40 is manually operable for selecting one of three stimulating methods, i.e., a single stimulation, a tetanic stimulation, and a train-of-four stimulation. The stimulating device 36 stimulates, according to the stimulating method selected through the operation of the input device 40, the wrist's skin via the two electrodes 14, 16 of the wrist band 12. In the single stimulation, the stimulating device 36 applies, to the electrodes 14, 16, a single-pulse electric current; in the tetanic stimulation, the stimulating device 36 applies, to the electrodes 14, 16, a 50 Hz electric current for five seconds; and in the train-of-four stimulation, the stimulating device 36 applies, to the electrodes 14, 16, a train of four successive electric-current pulses at intervals of 0.5 sec.

An electrocardiograph ("ECG") 42 includes a plurality of electrodes 44 adapted to be adhered to predetermined locations on the chest of the patient, and continuously detects, through the electrodes 44, an electrocardiogram ("ECG") waveform representing the active potential of the cardiac muscle of the heart of the patient. The ECG 42 supplies an ECG signal representing the detected ECG waveform, to the control device 28 via an A/D converter 46.

The ROM 32 stores, in advance, a predetermined relationship which is to be used by the control device 28 to determine an anesthetic depth, DA. A calibration switch 48 is manually operable for supplying, to the control device 28, a command signal to command the control device 28 to start a calibration operation for calibrating the predetermined relationship to be used to determine the anesthetic depth DA, so that the calibrated relationship may be suitable for each individual patient. A monitor-operation start/stop switch 50 is manually operable for alternately commanding the control device 28 to start, and stop, an anesthetic-depth monitor operation.

Figure 2:
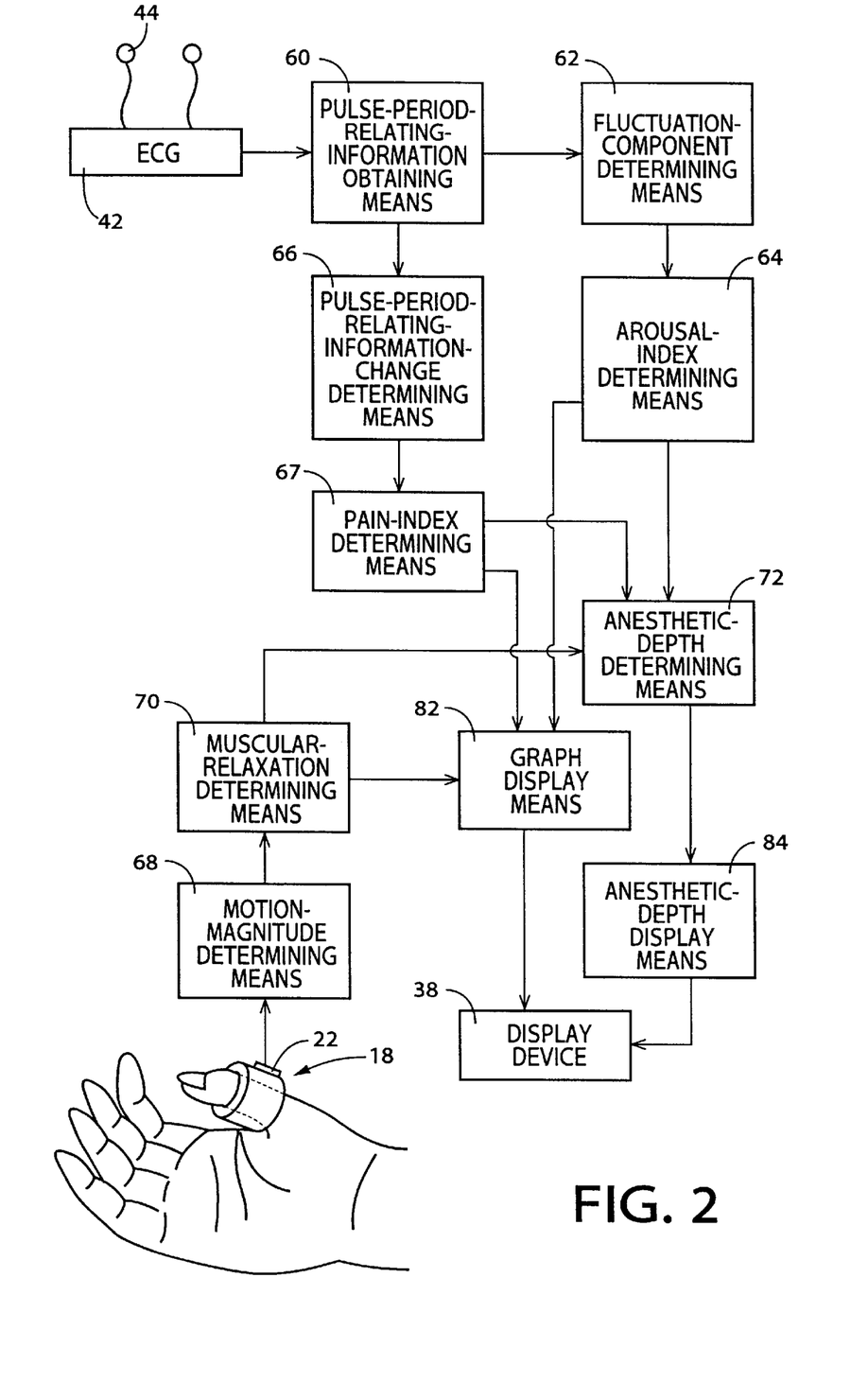
FIG. 2 is a diagrammatic view for explaining important control functions of a control device of the apparatus of FIG. 1.
Figure 3:
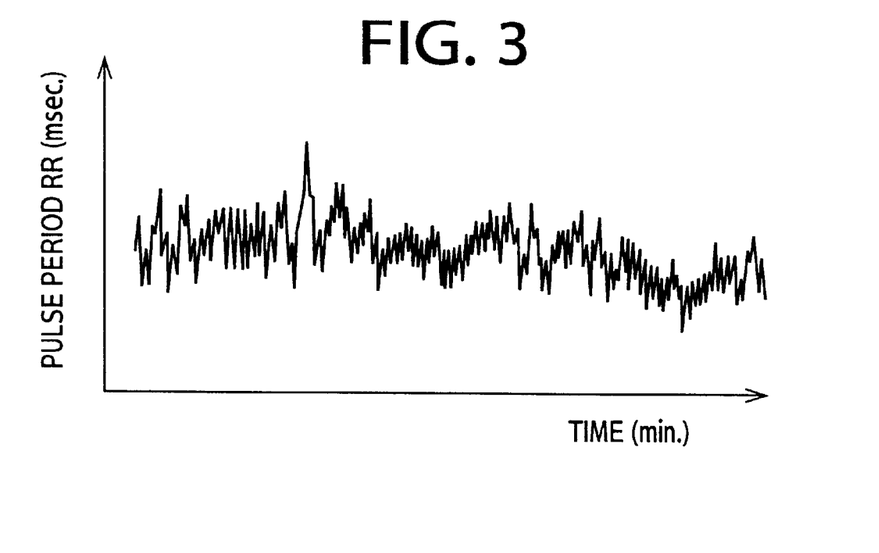
FIG. 3 is a graph showing fluctuations of pulse periods, RR, detected by the apparatus of FIG. 1.

FIG. 2 shows important control functions of the control device 28. A pulse-period-relating-information obtaining means 60 obtains, for each of successive heartbeat-synchronous pulses of the ECG waveform represented by the ECG signal supplied from the ECG 42, information relating to a pulse period at which the heart-beat-synchronous pulses periodically occur. For example, the obtaining means 60 determines, as a pulse period, RR, as a kind of the pulse-period-relating information, a time interval between respective periodic points or portions (e.g., respective R waves) of two successive heart beat-synchronous pulses. The obtaining means 60 may determine, as another sort of the pulse-period-relating information, a pulse or heart rate, HR, by dividing 60 by the pulse period RR. The pulse-period values RR successively determined by the obtaining means 60 contain fluctuations as shown in FIG. 3. That is, the batches of pulse-period-relating information successively obtained by the obtaining means 60 contain fluctuations.

Figure 4:
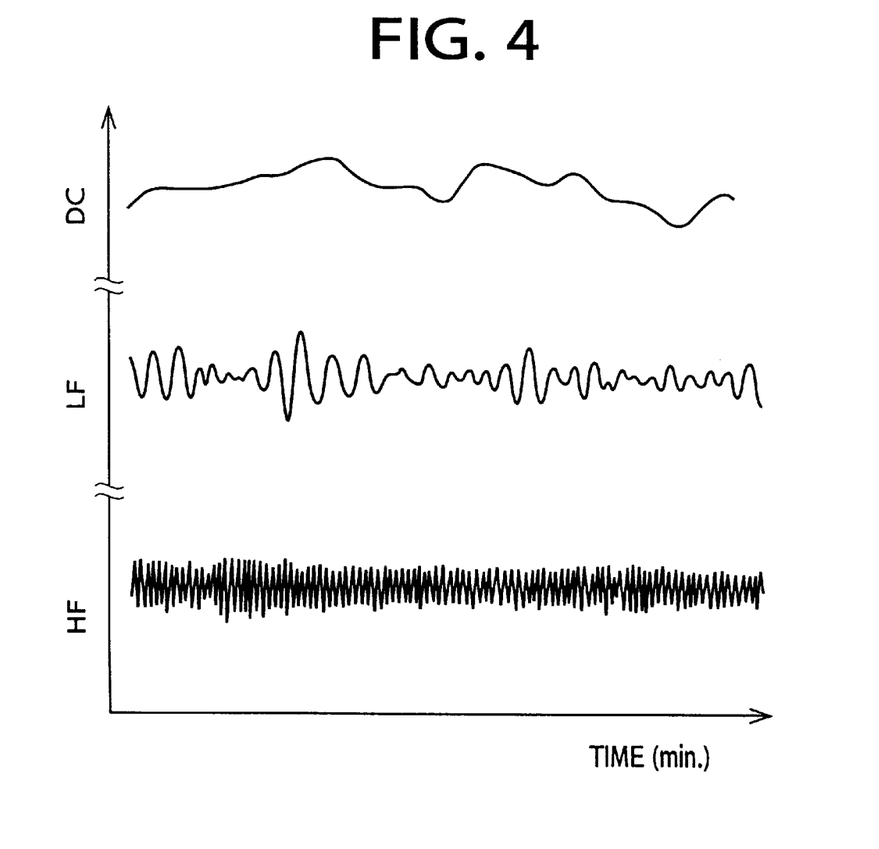
FIG. 4 is a graph showing a high-frequency component, HF, a low-frequency component, LF, and a direct-current or static component which are extracted from the fluctuations of the pulse periods RR detected by the apparatus of FIG. 1.

A fluctuation-component extracting means 62 extracts, from the fluctuations of the pulse-period values RR successively determined by the obtaining means 60, a high-frequency component, HF, that is produced in substantial synchronism with the respiration of the patient, and a low-frequency component, LF, that is lower than the high-frequency component HF and has frequencies equal to one third to one fourth of the frequency of the respiration of the patient. The extracting means 62 subjects the fluctuations of the pulse-period values RR to frequency analysis using, e.g., fast Fourier transform (FFT) method or auto-regression (AR) method, and determines, as the high-frequency component HF, a magnitude of a signal's peak occurring around the respiration frequency (e.g., 0.25 Hz) of the patient, and additionally determines, as the low-frequency component LF, a magnitude of another signal's peak occurring around a frequency range corresponding to one third to one fourth of the respiration frequency of the patient. FIG. 4 shows the high-frequency component HF, the low-frequency component LF, and a 0 Hz frequency component (i.e., direct-current component), DC, which are extracted from the fluctuations of the pulse period values RR shown in FIG. 3.

Figure 5:
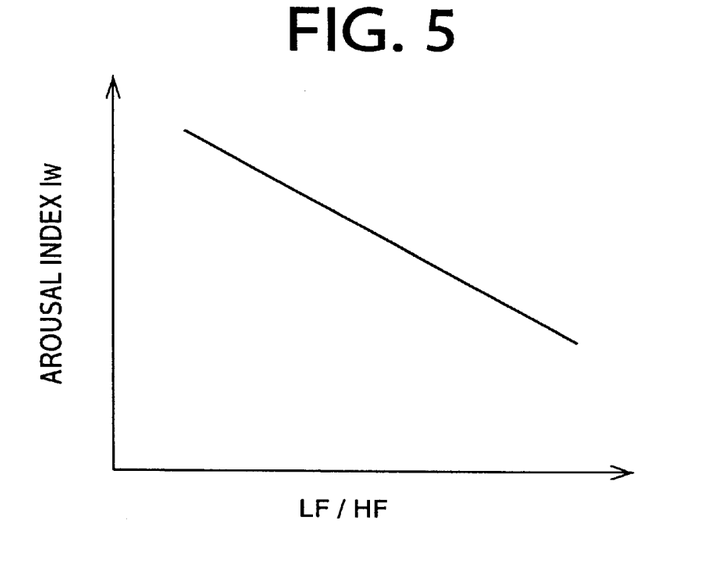
FIG. 5 is a graph showing a relationship which is used by the apparatus of FIG. 1 to determine an arousal index, $I_W$.

An arousal-index determining means 64 iteratively determines an arousal index, $I_W$, based on physical information which changes depending upon the current degree of arousal of the patient, that is, information relating to arousal. In the present embodiment, the arousal-index determining means 64 determines the arousal index $I_W$ based on the ratio, LF/HF, of the low frequency component LF to the high-frequency component HF both of which are determined by the fluctuation-component extracting means 62. For example, in the case where the standard ratio LF/HF of a low frequency component LF to a high-frequency component HF which are obtained by the extracting means 62 from a patient to whom an anesthetic agent has not been administered, is determined as a standard arousal index $I_W=1$, the current ratio LF/HF of a low frequency component LF to a high-frequency component HF which are obtained by the extracting means 62 from the patient during a surgical operation in which the patient is under anesthesia caused by the administration of the anesthetic agent, is determined, and the ratio or proportion of the current ratio LF/HF to the standard ratio LF/HF is determined as a current arousal index $I_W$ of the patient. Alternatively, the arousal-index determining means 64 may iteratively determine, according to a predetermined relationship between arousal index $I_W$ and ratio LF/HF, as shown in FIG. 5, a current arousal index $I_W$ of the patient based on the ratio LF/HF of a low frequency component LF to a high-frequency component HF both of which are iteratively determined by the extracting means 62. The ratio LF/HF is known as an index which can be used to evaluate the activity of sympathetic nerve system.

A pulse-period-relating-information-change determining means 66 iteratively determines a change (e.g., a rate of change or an amount of change) between the leading and trailing ones of a predetermined number of the successive pulse-period values RR as the batches of pulse-period-relating information successively obtained by the obtaining means 60. The pulse-period-relating information is known to be changeable when a living subject feels pain.

Figure 6:
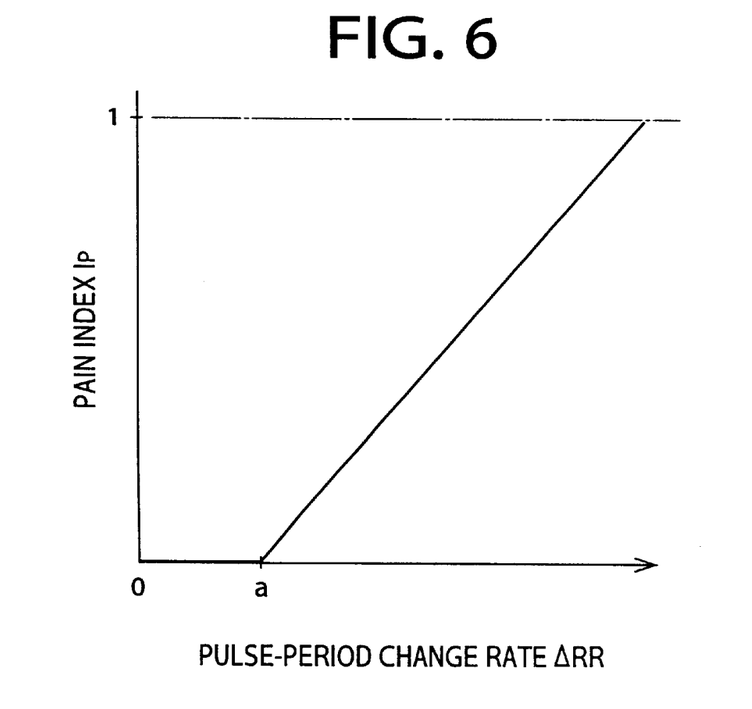
FIG. 6 is a graph showing a relationship which is used by the apparatus of FIG. 1 to determine a pain index, $I_P$.

A pain-index determining means 67 iteratively determines, according to a predetermined relationship between pain index, $I_P$, and pain-relating information, such as change of pulse-period-relating information, that is changeable when a living subject feels pain, a pain index $I_P$ of the patient that indicates a degree of pain actually felt by the patient, based on an actually obtained batch of pain-relating information. In the present embodiment, the pain-index determining means 67 iteratively determines, according to a predetermined relationship between pain index $I_P$ and rate of change, $\Delta RR$, of pulse period, as shown in FIG. 6, a pain index $I_P$ of the patient, based on an actual rate of change RR of the pulse-period values RR that is iteratively determined by the means 66. The relationship shown in FIG. 6 defines a pain index $I_P=0$ when the change rate $\Delta RR$ is not greater than a value, a, which is experimentally determined in advance to remove the fluctuations of the pulse-period values RR that are detected in the state in which no pain-causing stimuli are applied to the patient.

A motion-magnitude determining means 68 determines a magnitude of a motion of the thumb on which the cuff 18 is worn, based on the electric signal supplied from the pressure sensor 22 to the control device 28 when the stimulating device 36 electrically stimulates the wrist via the electrodes 14, 16 according to the stimulating method selected through the input device 40. When the stimulating device 36 electrically stimulates the ulnar nerve of the wrist, the thumb exhibits a reflex motion, thereby deforming the air bag 20, so that the pressure sensor 22 produces the electric signal representing a change of the air pressure in the air bag 20. Thus, the motion-magnitude determining means 68 can determine a magnitude of the motion of the thumb (i.e., reaction of the patient to the electric stimulus or stimuli), based on the electric signal supplied from the pressure sensor 22.

A muscular-relaxation-index determining means 70 iteratively determines a muscular-relaxation index, $I_R$, based on physical information that is changeable depending upon a degree of relaxation of the muscles of the patient, that is, muscular-relaxation-relating information. In the present embodiment, the muscular-relaxation-index determining means 70 iteratively determines a muscular-relaxation index $I_R$ based on a motion magnitude iteratively determined by the determining means 68. For example, in the case where a standard motion magnitude which is determined by the determining means 68 on a patient to whom a muscle relaxant has not been administered, is determined as a standard muscular-relaxation index $I_R=1$, a current motion magnitude which is iteratively determined by the determining means 68 on the patient to whom the muscle relaxant has been administered, is determined, and the ratio or proportion of the current motion magnitude to the standard motion magnitude is iteratively determined as a current muscular-relaxation index $I_R$. Alternatively, the muscular-relaxation-index determining means 70 may iteratively determine, according to a predetermined relationship between muscular-relaxation index $I_P$ and motion magnitude, a current motion magnitude of the patient based on a motion magnitude which is iteratively determined by the determining means 68.

An anesthetic-depth determining means 72 iteratively determines, based on the arousal index $I_W$ determined by the means 64, the pain index $I_P$ determined by the means 67, and the muscular-relaxation index $I_R$ determined by the means 70, an anesthetic depth DA of the patient according to a predetermined relationship between (A) anesthetic depth DA and (B) (b1) arousal index $I_W$, (b2) pain index $I_P$, and (b3) muscular-relaxation index $I_R$. This predetermined relationship may be a relationship between anesthetic depth DA and a linear or higher combination of three indexes $I_W$, $I_P$, and $I_R$; a neural network which has learned a relationship between anesthetic depth DA and three indexes $I_W$, $I_P$, and $I_R$; or a volume or an area of a solid which is defined by three indexes $I_W$, $I_P$, and $I_R$. In the last case, the volume or area of the solid may be a volume or a surface area of a triangular pyramid 80, as shown in FIG. 7, which is defined, in a three-dimensional space having a first axis 74 indicative of arousal index $I_W$, a second axis 76 indicative of pain index $I_P$, and a third axis 78 indicative of muscular-relaxation index $I_R$, by an origin, O, of the three axes 74, 76, 78, the arousal-index value $I_W$ determined by the means 64, the pain-index value $I_P$ determined by the means 67, and the muscular-relaxation-index value $I_R$ determined by the means 70; or a volume or a surface area of a rectangular parallelopiped which is defined by the origin O and the three index values $I_W$, $I_P$, $I_R$.

Figure 7:
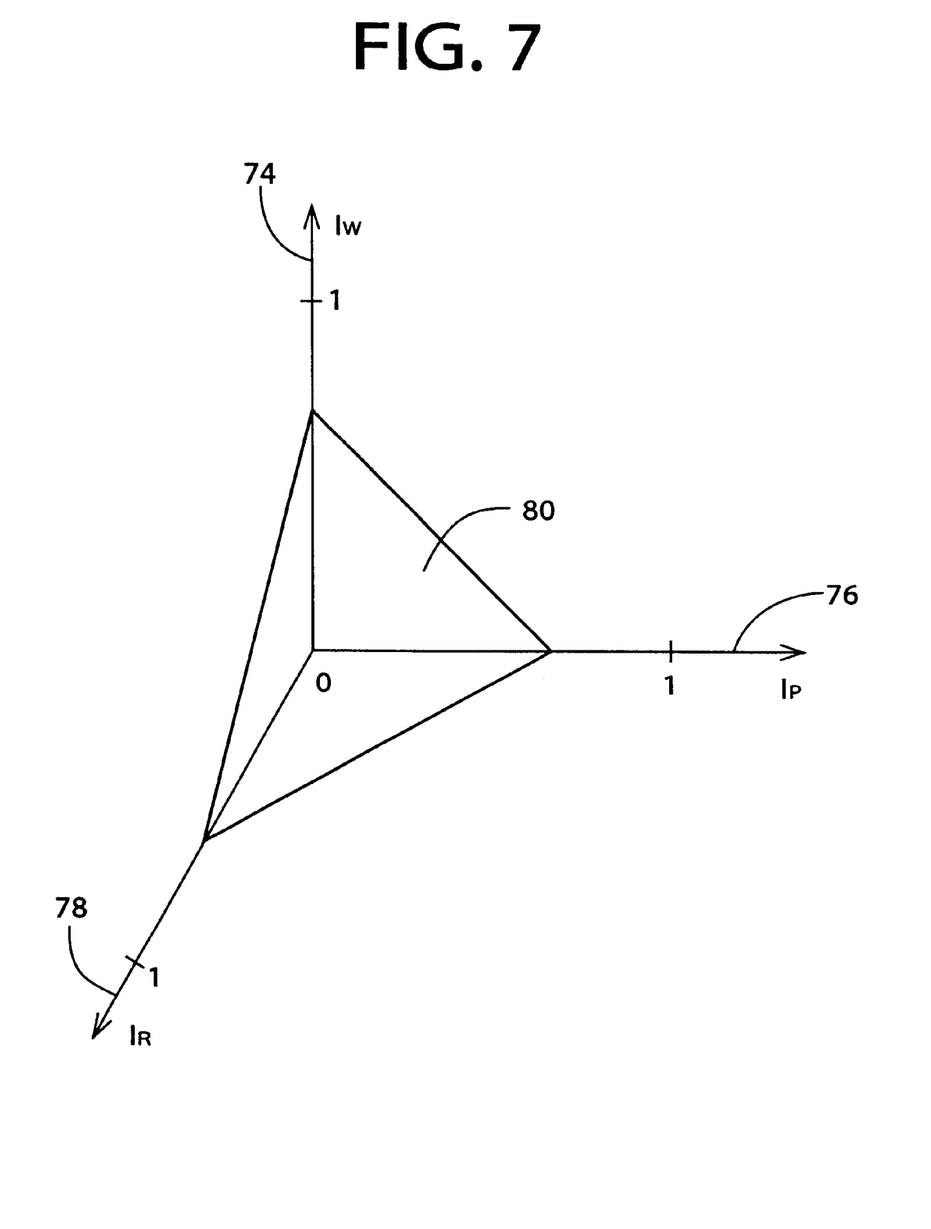
FIG. 7 is a three-dimensional graph showing the arousal index $I_W$, the pain index $I_P$, and a muscular-relaxation index, $I_R$, which are determined by the apparatus of FIG. 1.

A graph display means 82 controls the display device 38 to display, in the three-dimensional space having the three axes 74, 76, 78, shown in FIG. 7, the triangular pyramid 80 (or the rectangular parallelopiped) which is defined by the three index values $I_W$, $I_P$, $I_R$ which are iteratively determined by the three means 64, 67, 70.

An anesthetic-depth display means 84 controls the display device 38 to display, in digits, the anesthetic depth DA which is iteratively determined by the anesthetic-depth determining means 72.

Figure 8:
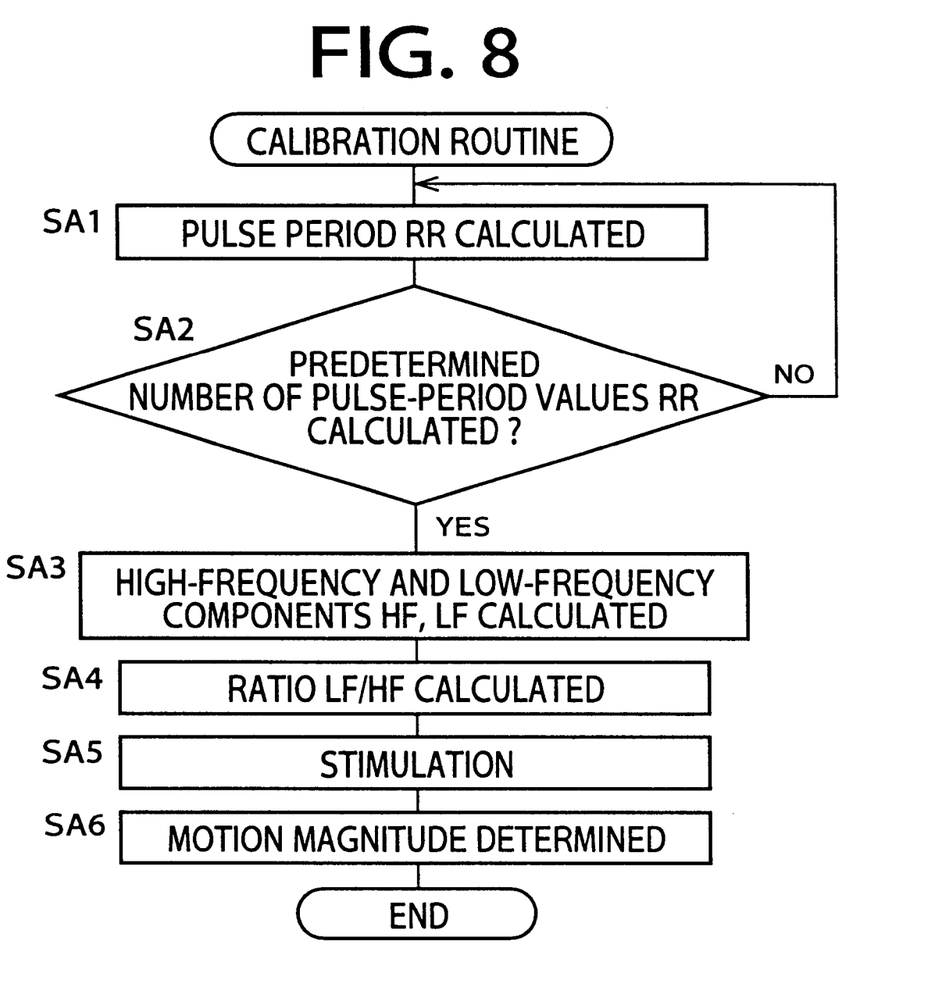
FIG. 8 is a flow chart representing a calibration routine as a control program according to which the control device of FIG. 2 is operated before an anesthetic agent is administered to a patient.

FIG. 8 shows a flow chart representing a calibration routine as a control program which is pre-stored in the ROM 32 and according to which the control device 28 is worked, upon operation of the calibration switch 48 before an anesthetic agent is administered to the patient, so that the predetermined relationship to be used to determine the anesthetic depth DA is calibrated to be suitable for each individual patient.

First, at Step SA1 corresponding to the pulse-period-relating-information obtaining means 60, the control device 28 determines, as a pulse-period value RR, a time interval between respective R waves of the last and second last heartbeat-synchronous pulses of the ECG waveform represented by the ECG signal supplied from the ECG 42. At the following step, Step SA2, the control device 28 judges whether it has determined, at Step SA1, a predetermined number (e.g., 30) of pulse-period values RR which are sufficient for analyzing the fluctuations of the pulse-period values RR. If a negative judgment is made at Step SA2, the control device 28 repeats Steps SA1 and SA2 to continue successively determining pulse-wave values RR.

Meanwhile, if a positive judgment is made at Step SA2, the control of the control device 28 goes to Step SA3 corresponding to the fluctuation-component extracting means 62. At Step SA3, the control device 28 subjects the timewise fluctuations of the predetermined number of pulse-period values RR determined at Step SA1, to the frequency analysis using, e.g., the fast Fourier transform (FFT) method or the auto-regression (AR) method, and determines, as the high-frequency component HF, a magnitude of a peak of a frequency-analysis spectrum signal that occurs around the respiration frequency (e.g., 0.25 Hz) of the patient, and determines, as the low-frequency component LF, a magnitude of another peak of the frequency-analysis spectrum signal that occurs around a frequency band (e.g., 0.07 Hz) corresponding to one third or one fourth of the respiration frequency of the patient.

At the following step, Step SA4, corresponding to the arousal-index determining means 64, the control device 28 determines a standard ratio LF/HF of the low-frequency component LF to the high-frequency component HF both of which are determined at Step SA3, and determines the thus determined standard ratio LF/HF as a standard arousal index $I_W=0$.

Step SA4 is followed by Step SA5 to operate the stimulating device 36 to electrically stimulate the wrist via the electrodes 14, 16 according to the stimulating method selected through the input device 40. When the wrist is electrically stimulated in this way, the thumb exhibits a reflex motion, thereby deforming the air bag 20 and changing the air pressure in the air bag 20.

At the following step, Step SA6, corresponding to the motion-magnitude determining means 68, the control device 28 calculates, based on the electric signal supplied from the pressure sensor 22, the change of the air pressure in the air bag 20, and calculates a standard magnitude of the reflex motion of the thumb based on the thus determined air-pressure change. The control device 28 determines the thus determined standard motion magnitude as a standard muscular-relaxation index $I_R=0$.

In the calibration routine of FIG. 8, it is not necessary to determine a pulse-period change rate $\Delta RR$ or a pain index $I_P$ because the relationship shown in FIG. 6 is widely applicable to all patients and it is not appropriate to cause each patient to feel pain before an anesthetic agent is administered to the patient. The standard pain index $I_P=1$ defined by the relationship of FIG. 6 corresponds to a pulse-period change rate $\Delta RR$ which would be obtained if each patient would feel pain before an anesthetic agent is administered to the patient. If each patient has his or her body cut or invaded by a surgeon during a surgical operation, the current pain index $I_P$ may take a value between 0 and 1 depending upon the current anesthetic depth DA of the patient.

Figure 9:
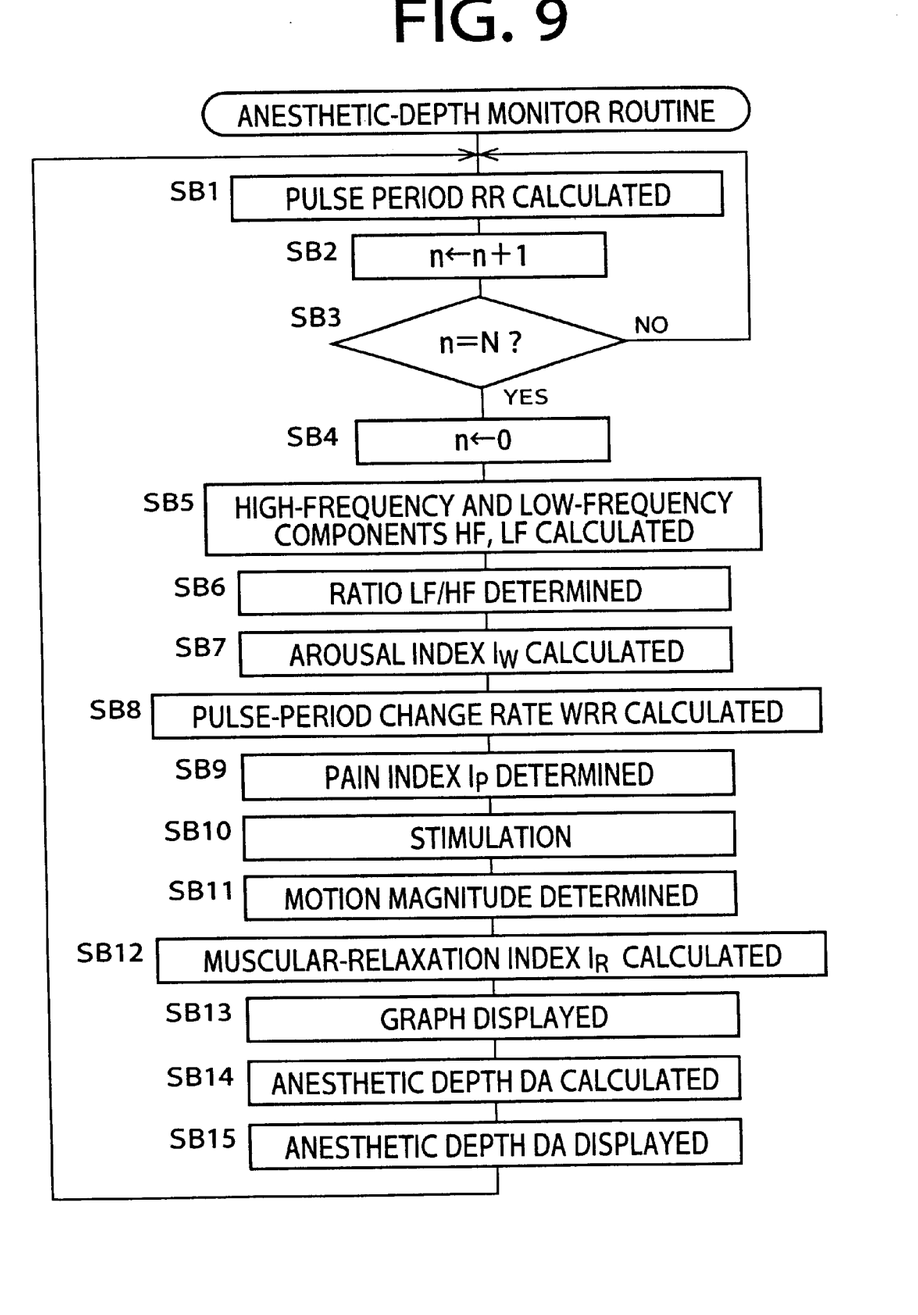
FIG. 9 is a flow chart representing an anesthetic-depth monitor routine as another control program according to which the control device of FIG. 2 is operated during a surgical operation in which the patient is under anesthesia caused by the administration of the anesthetic agent.

FIG. 9 is a flow chart representing an anesthetic-depth monitor routine as another control program according to which the control device 28 is operated upon operation of the monitor-operation start/stop switch 50 during the surgical operation in which the patient is under anesthesia caused by the administration of the anesthetic agent.

At Step SB1 corresponding to the pulse-period-relating-information obtaining means 60, the control device 28 determines, as a pulse-period value RR, a time interval between respective R waves of the last and second last heartbeat-synchronous pulses of the ECG waveform represented by the ECG signal supplied from the ECG 42. At the following step, Step SB2, the control device 28 increments a counter, n, by one. Step SB2 is followed by Step SB3 to judge whether the counter n is equal to a predetermined number, N, (e.g., N=5). Thus, the present monitor apparatus 10 determines one anesthetic-depth value DA for every predetermined number (N) of heartbeat-synchronous pulses of the ECG waveform.

If a negative judgment is made at Step SB3, the control device 28 repeats Steps SB1 to SB3 to continue successively determining pulse-period values RR. Meanwhile, if a positive judgment is made, the control goes to Step SB4 to reset the counter n to 0. Step SB4 is followed by Step SB5 corresponding to the fluctuation-component extracting means 62. At Step SB5, the control device 28 subjects the timewise fluctuations of the predetermined number (e.g., 30) of pulse-period values RR determined at Step SB1, to the frequency analysis, and determines a high-frequency component HF and a low-frequency component LF of the fluctuations, in the same manner as employed in Step SA3 of FIG. 8.

At the following step, Step SB6, the control device 28 determines the current ratio LF/HF of the low-frequency component LF to the high-frequency component HF both of which are determined at Step SB5.

At the following step, Step SB7, corresponding to the arousal-index determining means 64, the control device 28 determines the ratio or proportion of the current ratio LF/HF determined at Step SB6 to the standard ratio LF/HF determined at Step SA4 of FIG. 8, and determines the thus determined proportion as a current arousal index $I_W$. Thus, the current arousal index $I_W$ determined at Step SB7 falls within the range of 0 to 1.

At the following step, Step SB8, corresponding to the pulse-period-information-change determining means 66, the control device 28 determines, based on the pulse-period values RR determined at Step SB1, a rate of change, $\Delta RR$, of the current pulse-period value $RR_{CUR}$ determined at Step SB1 for the last or current heartbeat-synchronous pulse, from another pulse-period value $RR_{PRI}$ determined at Step SB1 for another pulse prior by a predetermined number (e.g., 1 or 5) of pulses from the current pulse, according to the following expression: $WRR=|(RR_{CUR}-RR_{PRI})/RR_{PRI}|$.

At the following step, Step SB9, corresponding to the pain-index determining means 67, the control device 28 determines, based on the pulse-period change rate $\Delta RR$ determined at Step SB8, a current pain index $I_P$ according to the predetermined relationship between $I_P$ and pulse-period change rate $\Delta RR$, shown in FIG. 6.

At the following steps, Steps SB10 and SB11, the control device 28 operates the stimulating device 36, and determines a magnitude of a motion of the thumb in response to the electric stimulus or stimuli applied by the device 36, in the same manners as those employed at Steps SA5, SA6 of FIG. 8.

At the following step, Step SB12, corresponding to the muscular-relaxation-index determining means 70, the control device 28 determines the ratio or proportion of the current motion magnitude determined at Step SB11 to the standard motion magnitude determined at Step SA6 of FIG. 8, and determines the thus determined proportion as a current muscular-relaxation index $I_R$. Thus, the current muscular-relaxation index $I_R$ determined at Step SB12 falls within the range of 0 to 1.

At the following step, Step SB13, corresponding to the graph display means 80, the control device 28 controls the display device 38 to display, in the three-dimensional graph, the current arousal index $I_W$ determined at Step SB7, the current pain index $I_P$ determined at Step SB9, and the current muscular-relaxation index $I_R$ determined at Step SB12, as shown in FIG. 7.

At the following step, Step SB14, corresponding to the anesthetic-depth determining means 72, the control device 28 determines a current anesthetic depth DA based on the current arousal index $I_W$ determined at Step SB7, the current pain index $I_P$ determined at Step SB9, and the current muscular-relaxation index $I_R$ determined at Step SB12. For example, in the case where a standard volume of a triangular pyramid (hereinafter, referred to as the "maximum triangular pyramid") which is defined, in the three-dimensional graph shown in FIG. 7, by the origin O, the standard arousal index $P_W=1$, the standard pain index $I_P=1$, and the standard muscular-relaxation index $P_W=1$, is determined as a standard anesthetic depth DA=100, the proportion of a volume of a triangular pyramid defined by the origin O, the current arousal index $I_W$ determined at Step SB7, the current pain index $I_P$ determined at Step SB9, and the current muscular-relaxation index $I_R$ determined at Step SB12, to the standard volume of the maximum triangular pyramid, is determined as a current anesthetic depth DA of the patient. Thus, the current muscular-relaxation index $I_R$ determined at Step SB14 falls within the range of 0 to 100. A greater index value DA indicates a shallower anesthesia or anesthetic depth.

At the following step, Step SB15, corresponding to the anesthetic-depth display means 84, the control device 28 controls the display device 38 to display, in digits, the anesthetic depth DA determined at Step SB14.

It emerges from the foregoing description that since the anesthetic-depth monitor apparatus 10 iteratively determines a current anesthetic-depth value DA based on a current arousal-index value $I_W$ determined at Step SB7, a current pain-index value $I_P$ determined at Step SB9, and a current muscular-relaxation-index value $I_R$ determined at Step SB12, the monitor apparatus 10 can monitor, with high reliability, the anesthetic depth DA of the patient during the surgical operation.

While the present invention has been described in its preferred embodiments, it is to be understood that the invention may otherwise be embodied.

For example, in the illustrated embodiment, the anesthetic-depth determining means 72 determines the anesthetic depth DA based on the three indexes, i.e., the arousal index $I_W$, the pain index $I_P$, and the muscular-relaxation index $I_R$. However, the anesthetic-depth determining means 72 may determine an anesthetic depth DA based on two of those three indexes, i.e., based on the arousal index $I_W$ and the pain index $I_P$, based on the arousal index $I_W$ and the muscular-relaxation index $I_R$, or based on the pain index $I_P$ and the muscular-relaxation index $I_R$. In the case where two of the three indexes are used to determine an anesthetic depth DA, a more reliable anesthetic depth DA can be determined than in the case where only one of the three indexes is used to determine an anesthetic depth DA.

In the illustrated embodiment, the arousal index $I_W$ is determined by using, as the arousal-relating information, the ratio LF/HF that is known as an index which is usable to evaluate the activity of sympathetic nerve system. However, it is possible to use, as the arousal-relating information, other indexes which are known as being usable to evaluate the activity of autonomic nerve system, a magnitude of an electroencephalography ("EEG") signal having a certain frequencies, an amount of motion of an eyeball, a diameter of a pupil, etc. It is possible to use, as the other indexes usable to evaluate the activity of autonomic nerve system, the ratio, $\Delta RR/\Delta BP_{SYS}$, of the pulse-period change rate $\Delta RR$ to a systolic-blood-pressure change rate, $\Delta BP_{SYS}$, a difference between a central-body temperature and a peripheral-body temperature, etc. In addition, it is possible to use, as the arousal-relating information, a bispectral index ("BIS") that is obtained by subjecting an EEG to bispectrum analysis and takes one value in the range of 0 to 100 indicating respective levels of consciousness.

In the illustrated embodiment, the pain index $I_P$ is determined by using, as the pain-relating information, the pulse-period-relating information. However, since blood pressure BP relates to pain, it is possible to use, as the pain-relating information, a change of blood-pressure-relating information which changes with change of the blood pressure. The change may be a rate of change with respect to time, or an amount of change. It is possible to use, as the blood-pressure-relating information, the blood pressure itself, a maximum angle or slope of an increasing portion of the waveform of a heartbeat-synchronous pulse of a pressure pulse wave, a velocity at, or a time in, which a pulse wave propagates between two different portions of a living subject, etc.

In the illustrated embodiment, the muscular-relaxation index $I_R$ is determined by using, as the muscular-relaxation-relating information, the amount of motion of the living subject in response to the electric stimulation applied thereto. However, since the muscular relaxation relates to the level of spontaneous respiration, it is possible to use, as the muscular-relaxation-relating information, the concentration of carbonic acid gas contained in expired gas.

In the illustrated embodiment, the monitor apparatus 10 is operated according to the calibration routine of FIG. 8, before an anesthetic agent is administered to a patient, so that the predetermined relationship to be used to determine an anesthetic depth DA is calibrated to be adapted for each individual patient. However, it is not essentially needed to calibrate the predetermined relationship for each individual patient. Even though the predetermined relationship may not be calibrated for each individual patient, it is possible to monitor, in a surgical operation, a relative change of the anesthetic depth of each patient.

It is to be understood that the present invention may be embodied with other changes, improvements and modifications that may occur to a person skilled in the art without departing from the scope and spirit of the invention defined in the appended claims.

What is claimed is:

1. An apparatus for monitoring an anesthetic depth of a living subject, comprising:

at least two devices of (a) an arousal-index determining device which determines an arousal index indicating a degree of arousal of the subject, (b) a pain-index determining device which determines a pain index indicating a degree of pain of the subject, and (c) a muscular-relaxation-index determining device which determines a muscular-relaxation index indicating a degree of muscular relaxation of the subject; and an anesthetic-depth determining means for determining, based on at least two indexes determined by said at least two devices, an anesthetic depth of the subject according to a predetermined relationship between anesthetic depth and said at least two indexes.

2. An apparatus according to claim 1, comprising the arousal-index determining device, wherein the arousal-index determining device comprises:

a pulse-wave sensor which detects a pulse wave including a plurality of heartbeat-synchronous pulses each of which is produced in synchronism with a heartbeat of the subject;

pulse-period-relating-information obtaining means for successively obtaining a batch of pulse-period-relating information relating to a pulse period at which said each heartbeat-synchronous pulse is produced in synchronism with said heartbeat of the subject;

means for determining a magnitude of a high-frequency component of fluctuations of the batches of pulseperiod-relating information successively obtained by the pulse-period-relating-information obtaining means, said high-frequency component having a high frequency substantially equal to a frequency of respiration of the subject;

means for determining a magnitude of a low-frequency component of the fluctuations of said batches of pulse-period-relating information, said low-frequency component having a low frequency substantially equal to a predetermined fraction of the frequency of respiration of the subject; and means for determining the arousal index based on a ratio of the magnitude of the low-frequency component to the magnitude of the high-frequency component.

3. An apparatus according to claim 2, wherein the pulse-wave sensor comprises an electrocardiograph which includes a plurality of electrodes adapted to be worn on the subject and which detects an electrocardiogram from the subject via the electrodes.

4. An apparatus according to claim 1, comprising the pain-index determining device, wherein the pain-index determining device comprises:

a pulse-wave sensor which detects a pulse wave including a plurality of heartbeat-synchronous pulses each of which is produced in synchronism with a heartbeat of the subject;

pulse-period-relating-information obtaining means for successively obtaining a batch of pulse-period-relating information relating to a pulse period at which said each heartbeat-synchronous pulse is produced in synchronism with said heartbeat of the subject;

pulse-period-relating-information-change determining means for determining a change of the batches of pulse-period-relating information successively obtained by the pulse-period-relating-information obtaining means; and means for determining the pain index based on the change determined by the pulse-period-relating-information-change determining means.

5. An apparatus according to claim 1, comprising the muscular-relaxation-index determining device, wherein the muscular-relaxation-index determining device comprises:

a stimulating device which applies a stimulus to a body portion of the subject;

a motion sensor which detects a motion of the body portion of the subject in response to the stimulus applied by the stimulating device; and means for determining the muscular-relaxation index based on a magnitude of the motion detected by the motion sensor.

6. An apparatus according to claim 1, further comprising a display device which displays said at least two indexes determined by said at least two devices.

7. An apparatus according to claim 1, further comprising a display device which displays the anesthetic depth determined by the anesthetic-depth determining means.

8. An apparatus according to claim 1, wherein the anesthetic-depth determining means comprises means for determining the anesthetic depth based on a product of said at least two indexes determined by said at least two devices.

9. An apparatus for monitoring an anesthetic depth of a living subject, comprising:

an arousal-index determining device which determines an arousal index indicating a degree of arousal of the subject;

a pain-index determining device which determines a pain index indicating a degree of pain of the subject;

a muscular-relaxation-index determining device which determines a muscular-relaxation index indicating a degree of muscular relaxation of the subject; and an anesthetic-depth determining means for determining, based on the determined arousal index, the determined pain index, and the determined muscular-relaxation index, an anesthetic depth of the subject according to a predetermined relationship between (A) anesthetic depth and (B) (b1) arousal index, (b2) pain index, and (b3) muscular-relaxation index.

10. An apparatus according to claim 9, further comprising a display device which displays, in a three-dimensional graph having a first axis indicative of arousal index, a second axis indicative of pain index, and a third axis indicative of muscular-relaxation index, the arousal index determined by the arousal-index determining device, the pain index determined by the pain-index determining device, and the muscular-relaxation index determined by the muscular-relaxation-index determining device.

11. An apparatus according to claim 9, wherein the anesthetic-depth determining means comprises means for determining the anesthetic depth based on a product of the determined arousal index, the determined pain index, and the determined muscular-relaxation index.

* * * * *